US006423306B2

(12) United States Patent
Caes et al.

(10) Patent No.: US 6,423,306 B2
(45) Date of Patent: *Jul. 23, 2002

(54) COSMETIC COMPOSITIONS CONTAINING DI-BLOCK, TRI-BLOCK, MULTI-BLOCK AND RADIAL BLOCK COPOLYMERS

(75) Inventors: Carolyn Caes, Mahwah; Gary G. Graves, Morganville; Mohamed G. Kanji, Edison; Margarita Montes de Oca, Union; Greg Norman, Woodbridge; Carl Orr, Scotch Plains; Paul Thau, Berkeley Heights, all of NJ (US)

(73) Assignee: L'Oreal SA, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/258,809

(22) Filed: Feb. 26, 1999

(51) Int. Cl.$^7$ .............................................. A61K 31/74
(52) U.S. Cl. ................. 424/78.02; 514/844; 514/845; 514/846; 514/847; 514/848; 424/401
(58) Field of Search ................ 424/78.02; 514/844–848

(56) References Cited

U.S. PATENT DOCUMENTS

| | | | |
|---|---|---|---|
| 3,827,999 A | 8/1974 | Crossland | 260/336 |
| 3,867,533 A | 2/1975 | Schmolka | 424/258 |
| 4,164,563 A | 8/1979 | Chang | 424/83 |
| 4,369,284 A | 1/1983 | Chen | 524/476 |
| 4,425,328 A | 1/1984 | Nabial | 424/68 |
| 4,716,183 A | 12/1987 | Gamarra et al. | 522/80 |
| 4,798,853 A | 1/1989 | Handlin, Jr. | 523/173 |
| 4,944,937 A | 7/1990 | McCall | 424/65 |
| 4,976,961 A | 12/1990 | Norbury et al. | 424/401 |
| 4,976,963 A | 12/1990 | Schricker et al. | 424/438 |
| 5,013,473 A | 5/1991 | Norbury et al. | 252/174.13 |
| 5,102,656 A | 4/1992 | Kasat | 424/66 |
| 5,152,991 A | 10/1992 | Vogel et al. | 424/401 |
| 5,169,626 A | 12/1992 | Tanner et al. | 424/66 |
| 5,221,534 A * | 6/1993 | DesLauriers et al. | 424/78.03 |
| 5,232,689 A | 8/1993 | Katsoulis et al. | 424/66 |
| 5,254,332 A | 10/1993 | Grezcyn et al. | 424/66 |
| 5,294,438 A | 3/1994 | Chang et al. | 424/73 |
| 5,302,381 A | 4/1994 | Greczyn et al. | 424/66 |
| 5,510,072 A | 4/1996 | Rosenqvist et al. | 264/184 |
| 5,539,021 A | 7/1996 | Pate et al. | 523/335 |
| 5,558,872 A | 9/1996 | Jones et al. | 424/78.03 |
| 5,578,299 A | 11/1996 | Starch | 424/78.03 |
| 5,688,842 A | 11/1997 | Pate, III et al. | 523/335 |
| 5,710,206 A | 1/1998 | Francis et al. | 524/505 |
| 5,711,940 A | 1/1998 | Kuentz et al. | 424/61 |
| 5,756,082 A | 5/1998 | Cashin et al. | 424/78.03 |
| 5,800,816 A | 9/1998 | Brieva et al. | 424/63 |
| 5,959,009 A * | 9/1999 | Konik et al. | 524/261 |
| 6,060,072 A | 5/2000 | Konik et al. | 424/401 |

FOREIGN PATENT DOCUMENTS

| | | |
|---|---|---|
| EP | 0 154 831 A2 | 9/1985 |
| EP | 0 299 718 | 1/1989 |
| EP | 0 154 831 B1 | 12/1990 |
| EP | 0 497 144 B1 | 9/1995 |
| EP | 0 749 746 B1 | 9/1997 |
| EP | 0 850 649 A1 | 7/1998 |
| EP | 0 925 780 A1 | 6/1999 |
| EP | 1 002 528 A1 | 5/2000 |
| FR | 2 357 244 | 2/1978 |
| FR | 2 710 646 | 4/1995 |
| JP | 53-094041 | 8/1978 |
| JP | 58-160381 | 9/1983 |
| JP | 62-249653 | 10/1987 |
| JP | 4-50234 | 2/1992 |
| WO | WO 88/01164 | 2/1988 |
| WO | WO 91/13839 | 9/1991 |
| WO | WO 94/12190 | 6/1994 |
| WO | WO 97/17058 | 5/1997 |
| WO | WO 97/17059 | 5/1997 |
| WO | WO 97/49352 | 12/1997 |
| WO | WO 98/38981 | 9/1998 |
| WO | WO 98/42298 | * 10/1998 |
| WO | WO 99/22710 | 5/1999 |
| WO | WO 99/22711 | 5/1999 |
| WO | WO 99/28429 | 6/1999 |
| WO | WO 00/26285 | 5/2000 |

OTHER PUBLICATIONS

Derwent English Abstract of European Patent Application No. 0 749 746 B1.
Abstract 114:108 976, XP002143304, "Film–forming Aerosol Preparations Containing ABA–type Triblock Thermoplastic Elastomers".
English Language Abstract of EP 0 925 780 A1.
English Language Abstract of EP 1 002 528 A1.
International Search Report dated Aug. 10, 2000.
English language Derwent Abstract of JP 4–50234.
English language Derwent Abstract of JP 62–249653.
English language Derwent Abstract of JP 58–160381.
English language Derwent Abstract of JP 53–094041.

* cited by examiner

Primary Examiner—Jose' G. Dees
Assistant Examiner—Konata M George
(74) Attorney, Agent, or Firm—Finnegan, Henderson, Farabow, Garrett & Dunner, L.L.P.

(57) ABSTRACT

The subject-matter of the present invention is a transfer-free composition comprising (a) at least one of a di-block, tri-block, multi-block and/or radial block copolymer and optionally (b) a film former or a mixture of film formers. The composition may comprise any one of a di-block, tri-block, multi-block or radial block copolymer or any mixture or blend of co-polymers. Cosmetic and pharmaceutical compositions of the invention result in a film with very good retention, good transfer resistant properties, and which does not migrate over time. The compositions have cosmetic properties which are improved in relation to those of the "transfer free" products of the prior art.

35 Claims, No Drawings

COSMETIC COMPOSITIONS CONTAINING DI-BLOCK, TRI-BLOCK, MULTI-BLOCK AND RADIAL BLOCK COPOLYMERS

The present invention relates to a composition, in particular a cosmetic composition, with transfer resistance, long wearing, and waterproof properties. The composition comprises, in particular, di-block, tri-block, multi-block and/or radial or star block copolymers. It also relates to cosmetic and pharmaceutical products containing this composition.

Many cosmetic compositions including pigmented cosmetics such as foundations, concealers, mascaras, lipsticks, and other cosmetic and sunscreen lotions leave soft oily films that can transfer quite easily. This means that the composition is capable of becoming deposited, at least in part, on certain supports with which it is brought into contact, such as, for example, a glass, a cup, an item of clothing or the skin. On becoming deposited, the composition leaves a mark on the support. The result is less than optimal persistence of the composition and it requires application to be repeated regularly.

There are several transfer resistant cosmetic compositions that are known in the art; however, the majority of these compositions can still be improved. So-called "transfer-free" make-up compositions known in the art generally comprise, among their constituent fatty substances, volatile oils, in particular volatile silicone oils and/or volatile hydrocarbon oils. Additionally, the majority of these transfer free compositions is tacky; thus, the application and spreadability of the compositions could still be improved.

For example, one reason for poor film formation is that a "transfer-free" make-up composition can require the use of a complex composition in which the oils are partially replaced by volatile solvents which evaporate on contact with the skin, leaving a layer composed essentially of waxes and/or resins, pigments, fillers and actives. Apart from the preparation difficulties associated with the use of volatile compounds, this solution can have the drawback of leading to a make-up effect of powdery and matte appearance.

Another problem that can be encountered with transfer free compositions is stability. Many film formers used in the art need to be gelled in a solvent in order to functions as a thickener. The resulting formulations can present a problem if the solvent in these gel thickeners tends to migrate out of the gel matrix causing instability of the formulation. The need therefore remains for a stable cosmetic composition which transfers little or not at all, that is to say a "transfer free" or transfer resistant composition which also possesses good cosmetic properties such as ease of application, comfort, ease of make-up removal, non greasy, non tacky, non draggy during and after application, and water resistance.

The present invention is a composition which can overcome these disadvantages and obtain a film having properties such as a very good adherence to the substrate, flexibility, wearability, good dry time, non tacky, good retention, non transfer, and low migration over time. Film formation occurs when the solvent evaporates at a rate that preferably allows the film to form continuously and free from imperfections. The composition of the present invention also has cosmetic properties which can be improved in relation to those of the "transfer free" products of the prior art.

The present invention relates to a transfer resistant composition comprising (a) an effective amount of at least one of a di-block, tri-block, multi-block and/or radial or star block copolymer film former. The composition may further comprise (b) an additional film former or a mixture of additional film formers. The composition may comprise any one of a di-block, tri-block, multi-block or radial or star block copolymer film former or any mixture or blend of co-polymer film formers. A preferred embodiment is a composition comprising a tri-block or a radial or star copolymer film former or a mixture thereof. This preferred embodiment may also comprise an additional film former or a mixture of additional film formers.

In a another preferred embodiment, the transfer resistant composition may comprise an effective amount of at least one copolymer film former selected from di-block, tri-block, multi-block, and radial or star copolymers, and at least one additional film former with the proviso that the additional film former is not selected from alkyl cycloalkylacrylate.

The transfer resistant compositions of the invention may be used in a variety of cosmetic and pharmaceutical products. An effective amount of di-block, tri-block, multi-block and/or radial or star block copolymer film former or additional film former in a cosmetic or pharmaceutical product is the amount necessary to obtain the desired degree of transfer resistance properties . One of skill in the art will be able to determine routinely the effective amount of block copolymer film former and additional film former depending on the application and the transfer resistance properties desired. One of skill in the art will also be able to determine routinely the amount of block copolymer film former, additional film former, and other ingredients needed to obtain a stable cosmetic or pharmaceutical product, depending on the application. A stable cosmetic or pharmaceutical product is one of sufficient stability to enable effective commercialization of the cosmetic or pharmaceutical product.

By way of background, suspending and thickening agents typically include waxes, silica gels, gums, clays, fumed silica, fatty acid soaps, and various hydrocarbon gels. Hydrocarbon gels comprising di-block, tri-block, multi-block and/or radial or star block copolymers are used in the art as gelling agents or suspending and dispersing agents. See U.S. Pat. No. 5,756,082, WO 98/42298, and EP 0 497 144 B1, the disclosures of which are hereby incorporated by reference. Copolymers of this type are known in the art to have advantageous properties when used as a suspension agent for various solids and liquids. See WO98/38981, the disclosure of which is hereby incorporated by reference.

In a preferred embodiment, the di-block, tri-block, multi-block and/or radial or star block copolymer film formers used in the invention contain at least two thermodynamically incompatible segments. A di-block is usually defined as A-B type or a hard segment (A) followed by a soft segment (B) in sequence. A tri-block is usually defined as a A-B-A type copolymer or a ratio of one hard, one soft, and one hard segment. Multiblock or radial or star copolymer film formers usually contain any combination of hard and soft segments, provided that there are both hard and soft characteristics. An example of a hard block copolymer segment is styrene, while examples of soft block copolymer segments are ethylene, propylene, and butylene or combinations thereof.

In another preferred embodiment, the copolymer film former of the present invention is chosen from the class of Kraton® rubbers (Shell Chemical Company) or from similar gelling agents. In a further preferred embodiment, the copolymer film former comprises Kraton® rubbers that are present in a gel in amounts from about 10 to about 20% concentration by weight. Kraton® rubbers are thermoplastic elastomers in which the polymer chains comprise a tri-block, di-block, or radial or star block configuration or numerous mixtures thereof. The Kraton® tri-block rubbers have polystyrene segments on each end of a rubber segment, while the Kraton® di-block rubbers have a polystyrene segment attached to a rubber segment. The Kratone® radial or star configuration, in a further preferred embodiment, may be a four-point or other multipoint star made of rubber with a polystyrene segment attached to each end of a rubber segment. The configuration of each of the Kraton® rubbers form separate polystyrene and rubber domains.

Each molecule of Kraton® rubber is said to comprise block segments of styrene monomer units and rubber monomer and/or co-monomer units. The most common structure for the Kraton® triblock copolymer is the linear A-B-A block type styrene-butadiene-styrene, styrene-isoprene-styrene, or styrene-ethylenebutylene-styrene. The Kraton® di-block is preferably the AB block type such as styrene-ethylenepropylene, styrene-ethylenebutylene, styrene-butadiene, or styrene-isoprene. The Kraton® rubber configuration is well known in the art and any block copolymer film former with a similar configuration is within the practice of the invention.

Other preferred embodiments include the use of block copolymer film formers comprising a styrene/butylene/ethylene/styrene copolymer (tri-block), an ethylene/propylene/styrene copolymer (radial or star block) or a mixture or blend of the two. (Some manufacturers refer to block copolymers as hydrogenated block copolymers, e.g. hydrogenated styrene/butylene/ethylene/styrene copolymer (tri-block) or hydrogenated ethylene/propylene/styrene copolymer (radial or star block), all of which are within the scope of the invention.) Specific examples include Versagel M5960, or Versagel M5970, all of which are available from Penreco of Houston Tex. and block copolymers available from Brooks Industries, such as Gel Base.

The block copolymer film former may preferably be formulated by dissolving the block copolymer in a hydrocarbon solvent. Hydrocarbons useful in the practice of the invention include but are not limited to mineral oils, mineral solvents, mineral spirits, petroleum, waxes, synthetic hydrocarbons, animal oils, vegetable oils, and mixtures of various hydrogen carbons. In a preferred embodiment, the block copolymer film former is formulated by dissolving the block copolymer in isododecane or a light paraffinic solvent. In another preferred embodiment, the block copolymer film former may be formulated by dissolving the block copolymer in a non-hydrocarbon solvent such as amyl acetate, butyl acetate, isobutyl acetate, ethyl acetate, propyl acetate or isopropyl acetate.

The solvent and solubility conditions for formulating a block copolymer film former from a block copolymer will be chosen by a person skilled in the art in order to prepare a composition which has the desired properties. One of ordinary skill in the art will be able to determine the solubility parameters and choose a solvent based on the block copolymer chosen for the envisaged application. More information regarding solubility parameters and solvents useful in the processing of specific block copolymers is available from the various manufacturers of block copolymers, e.g. Shell Chemical Company. Additional discussions of polymer solubility parameter concepts are presented in: *Encyclopedia of Polymer Science and Technology*, Vol. 3, Interscience, New York (1965) and *Encyclopedia of Chemical Technology*, Supp. Vol., Interscience, New York (1971), the disclosures of which are hereby incorporated by reference.

Preferably, the block copolymer film formers of the present invention are water insoluble, can be processed at room temperature, offer excellent adherence to the skin, and are tack free. It is preferred that the copolymer film former be present in the outer phase of any cosmetic formulation and at high concentrations. Additionally, it is preferred that the copolymer film former be compatible with the other raw materials of that phase.

In another preferred embodiment, the block copolymer film former may be combined in a formulation with an additional film former (b). This additional film former may improve smoothness or spreadability, water-resistance, transfer resistance properties, or other cosmetic or pharmaceutical properties desired by one of skill in the art.

Depending on the application, the concentration of block copolymer film former may vary considerably. One of skill in the art will be able to determine routinely the preferred concentration of block copolymer film former depending on the application and the transfer resistance properties desired. For example, for cosmetic foundations, the block copolymer film former or block copolymer film former mixtures may preferably be used in an amount from less than about 1% to about 30% by weight, and more preferably from about 1% to about 15% by weight. For eyeliner formulations, the block copolymer film former or block copolymer film former mixture preferably may vary from about 5% to about 70% by weight, and more preferably from about 20% to about 70% by weight. For lipstick formulations, the block copolymer film former or block copolymer film former mixture preferably may vary from about 1% to about 70% by weight, and more preferably from about 10% to about 70% by weight.

The preferred concentration of additional film formers may also be determined by one of skill in the art and can vary considerably based on the application. For example, for cosmetic emulsions, an additional film former or combination of additional film formers is preferably used in an amount from less than 1% to 15% by weight, and more preferably from 1% to 10% by weight. For eyeliner formulations, the additional film former or combination of additional film formers are preferably used in an amount from less than 0.5% to 15% by weight, more preferably from 1% to 10% by weight. For lipstick formulations, the additional film former or combination of additional film formers is preferably used in an amount from less than 0.5% to 15% by weight, more preferably from 1% to 10% by weight.

Examples of preferred additional film formers that may be used in the practice of the invention include: vinylpyrrolidone/vinyl acetate (PVP/VA) copolymers such as the Luviskol VA grades (all ranges) from BASF® Corporation and the PVP/VA series from ISP; acrylic fluorinated emulsion film formers including Foraperle® film formers such as Foraperle® 303 D from Elf Atochem although Foraperle® may not be preferable for some cosmetic formulations; GANEX® copolymers such as Butylated PVP, PVP/Hexadecene copolymer, PVP/Eicosene copolymer or tricontanyl; Poly (vinylpyrrolidone/diethylaminoethyl methacrylate) or PVP/Dimethylaminoethylmethacrylate copolymers such as Copolymer845; Resin ACO-5014 (Imidized IB/MA copolymer); other PVP based polymers and copolymers; Silicone gums; Cyclomethicone and Dimethicone crosspolymers (For example, Dow Corning® 2-9040, See U.S. Pat. No. 5,654,362, the disclosure of which is hereby incorporated by reference); trimethyl siloxysilicates such as SR 1000, SS4230, or SS4267 available from GE Silicones; alkyl cycloalkylacrylate copolymers (See WO98/42298 the disclosure of which is hereby incorporated by reference); or Mexomere® film formers and other allyl stearate/vinyl acetate copolymers (allyl stearate/VA copolymers); Polyolprepolymers such as PPG-12/SMDI copolymer, Polyolprepolymers such as PPG-12/SMDI copolymer, Poly(oxy-1,2-ethanediyl), $\alpha$-hydro-$\omega$-hydroxy-, polymer with 1,1'-methylene-bis-(4-isocyanatocyclohexane) available from Barnet; Avalure™ AC Polymers (Acrylates Copolymer) and Avalure™ UR polymers (Polyurethane Dispersions), available from BFGoodrich.

Additional film formers which also may be used within the framework of the invention include any film former chemistry known in the art such as: PVP, acrylates, and urethanes; synthetic polymers of the polycondensate type or free-radical type, or ionic type, polymers of natural origin and mixtures thereof or any other film formers known within the practice of the cosmetic and pharmaceutical arts which one skilled in the art may determine to be compatible.

In a further preferred embodiment of the invention, the cosmetic product is a water-in-oil emulsion or an oil-in-water emulsion. While at least one of the copolymer film former and/or the additional film formers of the invention may be in the water or in the oil phase, maximum efficacy has been demonstrated when at least one of the block copolymer film formers is in the oil phase. In a preferred embodiment, at least one of the block copolymer film formers is in the oil phase and at least one additional film formers is in the oil phase. In other embodiments of the invention, at least one additional film former may be in the oil phase, the water phase, or there may be at least one additional film former in both the water and oil phases.

Other compositions known in the art that are intended to leave a film on the skin or hair may also be added to the compositions of the invention, including emollients and other ingredients usually employed in the field envisaged. These added ingredients may include gels, oils, waxes, preservatives, thickener agents, solvents, surfactants, emollients and other ingredients that when incorporated into the formulation stay on top of the skin and do not strongly adhere to the substrate. Characteristics of some of these materials may include an oily feeling and increased spreadability, as observed with some esters and organic sunscreens. In embodiments where these materials are added to the formulations of the invention to enhance the spreadability and the emollience of the product, however, it is preferred that the above materials be present in low enough concentrations for the formulation to retain its transfer resistance properties. The choice of block copolymer film former, additional film former and their concentration may also be adjusted to vary the transfer resistance properties.

Other emollients that may preferably be used in the compositions of the invention include glycerine, propylene glycol, cyclomethicone, dimethicone, and emollients and other similar ingredients disclosed in the *International Cosmetic Dictionary and Handbook Vol* 2., more particularly the emollients disclosed on pages 1656–1661. The disclosure of the *International Cosmetic Dictionary and Handbook Vol* 2. is hereby incorporated by reference. In a preferred embodiment, emollients are present at a concentration of about 0.5% to about 8% by weight.

The compositions of the invention may further include the fatty substances, and/or waxes which are usually employed in the field of application envisaged or other formulation aids. The formulation aids include organic and organosilicone emulsifiers for water-in-oil Systems. Examples of organic emulsifiers include any ethoxylated surfactants known in the art such as Polysorbate-20, Laureth-7, and Laureth-4. Examples of organosilicone emulsifiers include cetyl dimethicone copolyol-polyglyceryl-4-isostearate-hexylaurate (ABIL WE 09) available from Goldschmidt Chemical Corporation, Cetyl Dimethicone Copolyol (ABIL® EM 90), (ABIL® EM 97), Laurylmethicone Copolyol (5200), Cyclomethicone (and) Dimethicone Copolyol (DC 5225 C) available from GE silicones, Cyclopentasiloxane & Dimethicone Copolyol (GE SF 1528) or any other formulation aids known by one of skill in the art. Representative fatty substances include silicones in esterified or unesterified liquid form or in esterified solid form, such as behenate dimethicone, nonsilicone fatty substances, such as oils, pastes and vegetable, mineral, animal and/or synthetic waxes. In a preferred embodiment, formulation aids are present in amounts from about 1% to about 15% concentration by weight.

These fatty substances may be selected variously by the person skilled in the art in order to prepare a composition which has the desired properties, for example, consistency or texture. In particular, the composition according to the invention may include at least one of the above mentioned waxes, so as to ensure a good mechanical strength, especially when the composition is in the form of a stick.

In another preferred embodiment, spherical compounds were chosen to enhance a smooth feeling when applied and spread onto the skin. Spherical compounds within the practice of the invention include polyurethane such as BPD 500, nylon 12, silica, polymethyl methacrylates and other acrylates or methacrylates and their esters, and other microspheres.

It is also possible to add to the composition of the invention any customary additive from the field of compositions to be applied in any cosmetic formulation including cosmetic foundations, eye liners, lipsticks, mascaras, eyeshadows, concealers, lotions or any other mentioned applications of the invention such as: thickening agents, for example clays, or organoclays, silicas, cellulose derivatives; hectorites; synthetic polymers such as an acrylic polymer or an associative polymer of the polyurethane type; gums and in particular xanthan gum; spreading agents; dispersants; preservatives, in particular water-soluble preservatives; antifoaming agents; wetting agents; UV-screening agents; perfumes; fillers; cosmetic or pharmaceutical active agents; moisturizers; vitamins and derivatives thereof; biological materials and derivatives thereof.

The present compositions may also possess the ability to enable processing of a formulation and/or a product with a large amount of a volatile solvent at a low temperature. In a preferred embodiment, a formulation comprising the compositions of the invention can be processed at a temperature of 55° C. or lower.

The compositions of the invention can provide excellent transfer resistance, long wearing and waterproofing properties in a broad range of applications. These applications include pigmented cosmetics, including foundations, concealers, mascaras, eye liners, lipsticks, eyeshadows; nail varnishes; hairsprays, gels and mousses, sunscreen lotions, moisturizing lotions, lotions with active ingredients, and fragrance. The products of the present invention can particularly be useful in any cosmetic or pharmaceutical application which relates to formation of a flexible film that adheres strongly to the skin or hair.

In a preferred embodiment, the compositions of the present invention can be used to hold or bind onto the substrate, topical coatings, actives and functional ingredients. The active or functional ingredients may include pigments, UV filters, moisturizing agents, fragrance, pharmaceutical agents and other active or functional ingredients known in the cosmetic or pharmaceutical arts.

The composition of the invention may additionally include any additive usually employed in the field envisaged such as antioxidants, perfumes, essential oils, stabilizers, cosmetic active substances, moisturizers, vitamins, essential fatty acids, lipophilic sunscreens, liposoluble polymers, and especially hydrocarbon polymers such as polyalkylenes and polyacrylates.

The person skilled in the art will of course take care to choose the optional additional compounds and/or their quantity is such a way that the advantageous properties of the composition according to the invention are not, or are substantially not, impaired by the envisaged addition.

The compositions of the present invention may also be effective in waterproofing. The compositions may therefore minimize washoff of the active or functional ingredients. The compositions may also retard dehydration of the skin by forming an occlusive film and reducing trans epidermal water loss.

In a preferred embodiment, the compositions can provide a barrier between the skin and the environment, entrapping in between the active and/or functional ingredients. The preferred composition and the barrier formed by said composition may boost the activity of the functional ingredients such as the SPF and UV light protection and/or block the effect of the humidity and the environment.

In pigmented products, the ratio of copolymer film formers and additional film formers can be adjusted for best adherence to the skin or hair and water resistance. An important consideration is the ratio of pigments to the amount of film formers. A pigment should be understood to mean inorganic or organic, white or coloured particles. Pigments that may be used in the practice of the invention include titanium dioxide, D & C Red No. 7 Calcium Lake, D & C Red No. 21 Aluminum Lake, Iron Oxides, FD & C Yellow No. 5 Aluminum Lake, FD & C Blue no. 1 Aluminum Lake and any other pigment or treated pigment known in the cosmetic arts.

Fillers and mothers-of-pearl may also be added to said formulations to modify the texture of the composition and the matteness/gloss effect. Fillers should be understood to mean lamellar or nonlamellar, inorganic or synthetic, colourless or white particles. Mothers-of pearl should be understood to mean irridescent particles produced especially by certain mollusks in their shell or else synthesized. Pearling agents that may be used in the practice of the invention include mica, iron oxides, titanium dioxide and any other pearling agent known in the cosmetic arts.

The subject of the invention includes any cosmetic formulation. A preferred subject of the invention relates to cosmetic foundations. In a preferred embodiment, the formulation of a cosmetic foundation contains thickening agents in an amount from about 0.1 to 10% concentration by weight and emollients in an amount from about 0.5% to 8% concentration by weight.

Another subject of the invention is mascara. Mascara employing the composition of the invention may produce increased stability and better adherence to keratin fibres. Mascara using the composition of the invention may also provide greater wear resistance, improved water resistance, and improved cosmetic properties.

A preferred embodiment of mascara comprises at least one block copolymer film former of the invention and an allyl stearate/vinyl acetate copolymer film former an example of which is a Mexomere® film former. In a further preferred embodiment, a Mexomere® film former is present in a concentration of about 0.5% to about 10% by weight.

A further subject of the invention includes lotions such as suntan lotion. Lotions employing the composition of the invention may provided increased transfer resistance and water resistance. Lotions using the composition may also provide greater wearability.

Another subject of the invention includes eyeliner products. Eyeliner employing the composition of the invention may produce increased stability and better adherence to eyelid tissue. Eyeliners using the composition of the invention may also provide greater water resistance and improved cosmetic properties.

A preferred embodiment of eyeliner comprises the block copolymer film formers of the invention and at least one allyl stearate/vinyl acetate copolymer film former. In a further preferred embodiment, the allyl stearate/vinyl acetate copolymer film former is a Mexomere® film former. In a another preferred embodiment, a Mexomere® film former is present in a concentration of about 0.5% to about 3.5% by weight.

In addition, eyeliners of the present invention may also include at least one of hydrocarbon gels or bentone type gels, waxes such as beeswax, carnauba wax and derivatives thereof, preservatives, and other ingredients such as propylene carbonate, isododecane, silica, silica silylate, petroleum distillates, polyethylene, preservatives, and pigments such as iron oxides, ultramarines, and black oxides. Another embodiment would further comprise at least one bentone type gel, such as Gel SS71, Gel EA2786, Quaternium-18 Bentonite, 38 CE, Gel ISD V or Gel ISD. The concentration of Bentone type gel preferably may range from less than about 1% to about 50% by weight.

Another subject of the invention is a make-up composition for the lips comprising a sufficient quantity of at least one block copolymer film former and optionally at least one additional film former, the quantity being sufficient to make it possible to obtain a transfer resistant film.

A make-up composition for the lips according to the invention makes it possible to obtain a homogeneous film which has a light texture and remains comfortable to wear throughout the day. The preferred film is not tacky or sticky, while being soft, supple, elastic and flexible on the skin. The film can have very good retention, no transfer, no migration, and no stain.

The packaging and application device for any subject of the invention may be chosen and manufactured by persons skilled in the art on the basis of their general knowledge, and adapted according to the nature of the composition to be packaged. Indeed, the type of device to be used may be in particular linked to the consistency of the composition, in particular to its viscosity; it may also depend on the nature of the constituents present in the composition, such as the presence of volatile compounds.

EXAMPLES OF COMPOSITION

Example 1

A water/oil emulsion cosmetic foundation containing the following was prepared:

| | |
|---|---|
| Oil Phase | |
| Emulsifiers & Volatile Silicones Cyclomethicone & Dimethicone Copolyol | 15% |
| Solvents | 20% |
| Pigments and Fillers | 11% |
| Rheological Additives | 1.1% |
| Film Formers | |
| Trimethyl Siloxy Silicate | 3% |
| Isododecane & Hydrogenated styrene-butylene-ethylene-styrene copolymer and Hydrogenated ethylene-propylene-styrene copolymer | 5% |
| Preservatives | 0.5% |
| Microspheres | 3% |
| Emollients | 3% |
| Aqueous Phase | |
| Deionized Water | 37.3% |
| Emulsifier | 0.2% |
| Electrolyte | 0.6% |
| Preservative | 0.3% |

Example 2

A water/oil emulsion cosmetic foundation containing the following was prepared:

| | |
|---|---|
| Oil Phase | |
| Emulsifiers & Volatile Silicones Cyclomethicone & Dimethicone Copolyol | 13% |
| Solvents | 15.8% |
| Pigments and Fillers | 11% |
| Rheological Additives | 1.1% |
| Film Formers | 12% |

-continued

| | |
|---|---|
| Isododecane & Hydrogenated styrene-butylene-ethylene-styrene copolymer and Hydrogenated ethylene-propylene-styrene copolymer | |
| Preservatives | 0.5% |
| Microspheres | 3% |
| Emollients | 3% |
| Aqueous Phase | |
| Deionized Water | 39.5% |
| Emulsifier | 0.2% |
| Electrolyte | 0.6% |
| Preservative | 0.3% |

Example 3

A water/oil emulsion cosmetic foundation containing the following was prepared:

| | |
|---|---|
| Oil Phase | |
| Emulsifiers & Volatile Silicones | 12.50% |
| Cyclomethicone & Dimethicone Copolyol | |
| Solvents | 15.6% |
| Pigments and Fillers | 11% |
| UV Filters | 2% |
| Rheological Additives | 0.77% |
| Film Formers | 12.5% |
| Isododecane & Hydrogenated styrene-butylene-ethylene-styrene copolymer and Hydrogenated ethylene-propylene-styrene copolymer | |
| Preservatives | 0.5% |
| Microspheres | 2.5% |
| Emollients | 2.5% |
| Aqueous Phase | |
| Deionized Water | 36.13% |
| Film Formers | 3% |
| PVP/VA Copolymer | |
| Emulsifier | 0.2% |
| Electrolyte | 0.6% |
| Preservative | 0.2% |

Example 4

A water/oil emulsion cosmetic foundation containing the following was prepared:

| | |
|---|---|
| Oil Phase | |
| Emulsifiers | |
| Laurylmethicone Copolyol | 2% |
| Solvents | 18% |
| Pigments and Fillers | 10.8% |
| UV Filters | 2% |
| Rheological Additives | 0.77% |
| Film Formers | 12.5% |
| Isododecane & Hydrogenated styrene-butylene-ethylene-styrene copolymer and Hydrogenated ethylene-propylene-styrene copolymer | |
| Preservatives | 0.5% |
| Microspheres | 2.5% |
| Emollients | 2.5% |
| Aqueous Phase | |
| Deionized Water | 44.09% |
| Film Formers | 3% |
| PVP/VA Copolymer | |
| Emulsifier | 0.2% |
| Electrolyte | 1% |
| Preservative | 0.2% |

Example 5

A water/oil emulsion cosmetic foundation containing the following was prepared:

| | |
|---|---|
| Oil Phase | |
| Emulsifiers | |
| Cetyl Dimethicone Copolyol Hexylaurate | 5% |
| Solvents | 17.5% |
| Pigments and Fillers | 11% |
| Film Formers | 25% |
| Isododecane & Hydrogenated styrene-butylene-ethylene-styrene copolymer and Hydrogenated ethylene-propylene-styrene copolymer | |
| Preservatives | 0.5% |
| Microspheres | 3% |
| Emollients | 3% |
| Aqueous Phase | |
| Deionized Water | 33.9% |
| Emulsifier | 0.2% |
| Electrolyte | 0.6% |
| Preservative | 0.3% |

Example 6

A water/oil emulsion cosmetic foundation containing the following was prepared:

| | |
|---|---|
| Oil Phase | |
| Emulsifiers | 2.0% |
| Laurylmethicone Copolyol | |
| Solvents | 16.6% |
| Volatile Silicone | 5% |
| Pigments and Fillers | 15.7% |
| Rheological Additives | 0.7% |
| Film Formers | 12.5% |
| Isododecane & Hydrogenated styrene-butylene-ethylene-styrene copolymer and Hydrogenated ethylene-propylene-styrene copolymer | |
| Preservatives | 0.1% |
| Microspheres | 2.5% |
| Emollients | 2.5% |
| Aqueous Phase | |
| Deionized Water | 38% |
| Film Former | 3% |
| PVP/VA Copolymer | |
| Surfactant | 0.2% |
| Electrolyte | 1.0% |
| Preservative | 0.2% |

Example 7

Mascara

| Ingredient | % |
|---|---|
| Petroleum Distillates | 48.63 |
| Pigments | 6.00 |

-continued

| Ingredient | % |
| --- | --- |
| Bentone | 5.02 |
| Solvent | 9.80 |
| Isododecane & Hydrogenated styrene-butylene-ethylene-styrene copolymer and Hydrogenated ethylene-propylene-styrene copolymer | 5.00 |
| Starch | 0.76 |
| Propylene Carbonate | 1.65 |
| Waxes | 13.69 |
| Allyl Stearate/Vinyl Acetate Copolymer | 2.21 |
| Polyvinyl Laurate | 0.74 |
| Pigment Dispersing agent | 2.50 |
| Water | 2.49 |
| Preservatives | 0.01 |
| Filler | 1.50 |

Example 8

Mascara

| Ingredient | % |
| --- | --- |
| Waxes | 13.5 |
| Stearic Acid | 4.00 |
| Preservatives | 0.75 |
| PVP/Eicosene Copolymer | 1.00 |
| Allyl Stearate/Vinyl Acetate Copolymer | 1.00 |
| Water | 50.95 |
| Aqueous Thickener | 0.30 |
| Pigment Dispersing Agent | 0.15 |
| Pigments | 8.00 |
| PVP | 1.00 |
| Butylene Glycol | 3.00 |
| Tri-ethanol Amine | 2.00 |
| Simethicone | 0.10 |
| Isododecane & Hydrogenated styrene-butylene-ethylene-styrene copolymer and Hydrogenated ethylene-propylene-styrene copolymer | 5.00 |
| Isododecane | 1.75 |
| Silica | 2.00 |
| Polyurethane | 0.50 |
| Water | 1.00 |
| Alcohol | 5.00 |

Example 9

Suntan Lotion SPF 15

| Ingredient | Weight |
| --- | --- |
| Cetyl Dimethicone Copolyol-polyglyceryl-4-isostearate-hexylaurate | 5 |
| Isododecane & Hydrogenated styrene-butylene-ethylene-styrene copolymer and Hydrogenated ethylene-propylene-styrene copolymer | 200 |
| Isododecane | 144.65 |
| Octylmethoxycinnamate | 70 |
| Oxybenzone | 30 |
| Propylene Glycol | 30.06 |
| Polyurethane | 30 |
| Distilled Water | 370.36 |
| Polysorbate 20 | 2.02 |
| Electrolytes | 6.08 |
| Preservatives | 9.13 |

Example 10

Lipstick

| Ingredient | Weight |
| --- | --- |
| Ethylene/Propylene Copolymer | 11.00 |
| PVP/Hexadecene copolymer | 0.50 |
| Acrylates copolymer | 0.50 |
| Isododecane & Hydrogenated styrene-butylene-ethylene-styrene copolymer and Hydrogenated ethylene-propylene-styrene copolymer | 10.00 |
| Waxes | 7.50 |
| Silicone Emollients | 38.75 |
| Ester Emollients | 16.75 |
| Tocopherol | 0.10 |
| Preservatives | 0.40 |
| Pigments | 14.50 |

Example 11

EYELINER

| Ingredient | % |
| --- | --- |
| A | |
| Allyl Stearate/VA copolymers | 3.60 |
| Waxes | 2.90 |
| Preservatives | 0.30 |
| Isododecane & Hydrogenated styrene-butylene-ethylene-styrene copolymer and Hydrogenated ethylene-propylene-styrene copolymer | 25.00 |
| Isododecane | 43.93 |
| B | |
| Bentone | 3.85 |
| C | |
| Pigments | 19.00 |
| Filler | 0.17 |
| D | |
| Propylene Carbonate | 1.15 |

Procedure

Combine A heat to 70–75 C. while stirring, add B and homogenize for 5 min. on Silverson; add C and continue to homogenize for 10 more min.; add D and homogenize 15 more min.; cool to 30–35 while stirring.

Example 12

EYELINER

| Ingredient | % |
| --- | --- |
| A | |
| Trimethyl Siloxy Silicate | 10.00 |
| Isododecane | 41.43 |
| B | |
| Preservatives | 0.40 |
| Isaododecane & Hydrogenated styrene-butylene-ethylene-styrene copolymer and Hydrogenated ethylene-propylene-styrene copolymer | 25.00 |
| C | |
| Bentone | 3.00 |

-continued

| Ingredient | % |
|---|---|
| D | |
| Pigments | 17.17 |
| E | |
| Propylene Carbonate | 1.00 |

Procedure

Combine A, add B and mix until uniform; add C homogenize for 5 min.; add D and homogenize 5 more min.; add E and continue to homogenize 5 more min.

Example 13

EYELINER

| Ingredient | % |
|---|---|
| A | |
| Preservatives | 0.40 |
| Bentone | 42.74 |
| Petroleum Distillates | 23.54 |
| Pigments | 18.05 |
| Isododecane & Hydrogenated styrene-butylene-ethylene-styrene copolymer and Hydrogenated ethylene-propylene-styrene copolymer | 5.00 |
| Polyethylene | 2.85 |
| B | |
| Waxes | 3.80 |
| C | |
| Filler | 0.20 |
| D | |
| Propylene Carbonate | 1.00 |

Procedure

Combine A and heat to 92–98 C. mix until uniform; combine B & heat to 85–90 C. mix until uniform; add B to A and homogenize 30 min. 90–95 C.; cool to 50 C. then add C and continue to homogenize for 10 more min.; add D and homogenize 15 more min.;; cool to 30–35 C. w/mixing.

Example 14

EYELINER

| Ingredient | % |
|---|---|
| A | |
| Isododecane | 40.47 |
| Isododecane & Hydrogenated styrene-ethylene-butylene-styrene copolymer | 28.00 |
| Pigments | 18.00 |
| Bentone | 4.25 |
| Filler | 0.10 |

-continued

| Ingredient | % |
|---|---|
| B | |
| Preservatives | 0.40 |
| Allyl Stearate/VA Copolymer | 3.60 |
| Waxes | 2.90 |
| C | |
| Propylene Carbonate | 1.28 |

Procedure

Combine B and heat to 70–75 C.; in a separate beaker, combine A & homoginize(35%) for 35 min, heating to 65 C. during the last 15 min; add B to A & continue to homoginize (35%) for 5 min. heating to 70–75 C.; add C & continue to homoginize (45–50%) for 30 min. maintaining temperature between 75–80 C.; cool while stirring to 30–35 C.

We claim:

1. A transfer resistant cosmetic composition comprising an effective amount of at least one radial block copolymer film former
    with the proviso that said transfer resistant cosmetic composition does not also contain a tri-block or di-block copolymer.
2. A transfer resistant cosmetic composition of claim 1 wherein said composition further comprises at least one additional film former.
3. A transfer resistant cosmetic composition comprising an effective amount of at least one tri-block copolymer film former
    with the proviso that said transfer resistant cosmetic composition does not also contain a di-block, multi-block or radial copolymer.
4. A transfer resistant cosmetic composition of claim 3 wherein said composition further comprises at least one additional film former.
5. A transfer resistant cosmetic product comprising a water/oil emulsion foundation, said emulsion comprising an effective amount of at least one radial block copolymer film former
    with the proviso that said transfer resistant cosmetic composition does not also contain a tri-block or di-block copolymer.
6. A transfer resistant cosmetic product of claim 5 wherein said emulsion further contains at least one additional film former.
7. A transfer resistant cosmetic product of claim 6 wherein said additional film former is an Allyl Stearate/VA copolymer film former.
8. A transfer resistant cosmetic product of claim 5 wherein the water phase of said water/oil emulsion further comprises at least one film former.
9. A transfer resistant cosmetic product of claim 8 wherein said additional film former of said water phase is PVP/VA copolymer film former.
10. A transfer resistant cosmetic product comprising a water/oil emulsion foundation, said emulsion comprising an effective amount of at least one tri-block copolymer film former and at least one additional film former, wherein said at least one additional film former is not a block copolymer film former.
11. A transfer resistant cosmetic product of claim 10 wherein said additional film former is an Allyl Stearate/VA copolymer film former.
12. A transfer resistant cosmetic product of claim 10 wherein the water phase of said water/oil emulsion further comprises at least one film former.

13. A transfer resistant cosmetic product of claim 12 wherein said film former of said water phase is PVP/VA copolymer film former.

14. A transfer resistant eyeliner product comprising an effective amount of at least one radical block copolymer film former with the proviso that said transfer resistant cosmetic composition does not also contain a tri-block or di-block copolymer.

15. A transfer resistant eyeliner product of claim 14 wherein said product further comprises at least one additional film former.

16. A transfer resistant eyeliner product of claim 15 wherein said additional film former is an Allyl Stearate/VA copolymer film former.

17. A transfer resistant eyeliner product of claim 15 wherein said product further comprises organo-clays.

18. A transfer resistant eyeliner product comprising an effective amount of at least one tri-block copolymer film former with the proviso that said transfer resistant cosmetic composition does not also contain a di-block, multi-block or radial copolymer.

19. A transfer resistant eyeliner product of claim 18, wherein said product further comprises at least one additional film former.

20. A transfer resistant eyeliner product of claim 19 wherein said additional film former is an Allyl Stearate/VA copolymer film former.

21. A transfer resistant eyeliner product of claim 19 wherein said product further comprises organo-clays.

22. A transfer resistant mascara product comprising an effective amount of at least one radical block copolymer film former with the proviso that said transfer resistant cosmetic composition does not also contain a tri-block or di-block copolymer.

23. A transfer resistant mascara product of claim 22 wherein said product further comprises at least one additional film former.

24. A transfer resistant mascara product of claim 23 wherein said additional film former is an Allyl Stearate/VA copolymer film former.

25. A transfer resistant mascara product comprising an effective amount of at least one tri-block copolymer film former with the proviso that said transfer resistant cosmetic composition does not also contain a di-block, multi-block or radial copolymer.

26. A transfer resistant mascara product of claim 25, wherein said product further comprises at least one additional film former.

27. A transfer resistant mascara product of claim 26 wherein said additional film former is an Allyl Stearate/VA copolymer film former.

28. A transfer resistant resistant lotion comprising an effective amount of at least one radical block copolymer film former with the proviso that said transfer resistant cosmetic composition does not also contain a tri-block or di-block copolymer.

29. A transfer resistant lotion of claim 28 wherein said product further comprises at least one additional film former.

30. A transfer resistant lotion comprising an effective amount of at least one tri-block copolymer film former with the proviso that said transfer resistant cosmetic composition does not also contain a di-block, multi-block or radial copolymer.

31. A transfer resistant lotion of claim 30, wherein said product further comprises at least one additional film former.

32. A transfer resistant lipstick product comprising an effective amount of at least one radial block copolymer film former with the proviso that said transfer resistant cosmetic composition does not also contain a tri-block or di-block copolymer.

33. A transfer resistant lipstick product of claim 32 wherein said product further comprises at least one additional film former.

34. A transfer resistant lipstick product comprising an effective amount of at least one tri-block copolymer film former with the proviso that said transfer resistant cosmetic composition does not also contain a di-block, multi-block or radial copolymer.

35. A transfer resistant lipstick product of claim 34, wherein said product further comprises at least one additional film former.

* * * * *

UNITED STATES PATENT AND TRADEMARK OFFICE
CERTIFICATE OF CORRECTION

PATENT NO. : 6,423,306 B2
DATED : July 23, 2002
INVENTOR(S) : Carolyn Caes et al.

It is certified that error appears in the above-identified patent and that said Letters Patent is hereby corrected as shown below:

Column 16,
Line 10, delete the second occurrence of "resistant".

Signed and Sealed this

Twenty-sixth Day of November, 2002

*Attest:*

*Attesting Officer*

JAMES E. ROGAN
*Director of the United States Patent and Trademark Office*